(12) United States Patent
Fujii et al.

(10) Patent No.: US 8,137,101 B2
(45) Date of Patent: Mar. 20, 2012

(54) DETACHABLE STOPPER FOR DENTAL DRILL

(75) Inventors: Naoto Fujii, Itabashi-ku (JP); Yoshihiro Sakaguchi, Itabashi-ku (JP)

(73) Assignee: GC Corporation, Tokyo (JP)

( * ) Notice: Subject to any disclaimer, the term of this patent is extended or adjusted under 35 U.S.C. 154(b) by 182 days.

(21) Appl. No.: 12/435,649

(22) Filed: May 5, 2009

(65) Prior Publication Data

US 2009/0291411 A1 Nov. 26, 2009

(30) Foreign Application Priority Data

May 21, 2008 (JP) ................. 2008-133464

(51) Int. Cl.
- *A61C 3/00* (2006.01)
- *A61C 5/02* (2006.01)
- *A61C 3/02* (2006.01)
- *A41F 1/00* (2006.01)

(52) U.S. Cl. ............ 433/75; 433/102; 433/165; 24/456; 24/569; 408/202

(58) Field of Classification Search .................... 433/72, 433/75, 102, 165; 606/96–97, 102, 172; 411/540, 546, 80.1–80.6; 24/456, 535, 536, 24/569; 408/202; 407/50, 90, 109; 82/160; 403/362

See application file for complete search history.

(56) References Cited

U.S. PATENT DOCUMENTS

| | | | | |
|---|---|---|---|---|
| 1,818,627 A | * | 8/1931 | Kerr ........................... | 433/164 |
| 3,562,913 A | * | 2/1971 | Saffro .............................. | 433/75 |
| 4,505,010 A | * | 3/1985 | Arenhold ........................ | 24/456 |
| 5,087,161 A | * | 2/1992 | Gunn ............................ | 411/433 |
| 5,429,504 A | * | 7/1995 | Peltier et al. .................. | 433/165 |
| 7,134,251 B2 | * | 11/2006 | Zurn et al. ..................... | 52/514 |
| 7,175,428 B2 | * | 2/2007 | Nicholson ....................... | 433/11 |
| 2006/0188840 A1 | * | 8/2006 | Verban ............................ | 433/75 |

FOREIGN PATENT DOCUMENTS

| | | |
|---|---|---|
| EP | 0 171 830 A1 | 2/1986 |
| EP | 0 515 274 A1 | 11/1992 |
| JP | 2005-518834 | 6/2005 |
| WO | WO 03/071972 A1 | 9/2003 |

\* cited by examiner

*Primary Examiner* — Todd Manahan
*Assistant Examiner* — Yogesh Patel
(74) *Attorney, Agent, or Firm* — Oblon, Spivak, McClelland, Maier & Neustadt, L.L.P.

(57) ABSTRACT

To provide a detachable stopper fixed on a spindle part of a dental drill to regulate the depth of an implant fixture embedding hole in an implant treatment, the detachable stopper includes a stopper main body 1 being made of an elastically deformable metal material, having a cylindrical shape, having a slightly smaller inner diameter than an outer diameter of the spindle part, having a slit part 1*a* formed along an axial overall length from an outer peripheral face to an inner peripheral face to have an opening, and having a diameter expanding tool insertion part 1*b* bored at an axial center of the slit part 1*a*, and a diameter expanding tool 2 to be inserted into the diameter expanding tool insertion part 1*b* to expand the inner diameter of the stopper main body 1 to be larger than the outer diameter of the spindle part.

12 Claims, 6 Drawing Sheets

1a 1a  1b

DETACHABLE STOPPER FOR DENTAL DRILL

BACKGROUND OF THE INVENTION

1. Field of the Invention

The present invention relates to a detachable stopper for a dental drill for regulating a depth of a hole. The dental drill is for boring an implant fixture embedding hole in an implant treatment and has a blade part on the front end side of the spindle part. The spindle part has a diameter shrunk part formed as a mounting part for preventing slipping-off to a dental hand piece at a rear end thereof, or a cylindrical shape having an equal diameter without having the diameter shrunk part. The detachable stopper is externally fitted to and fixed at a position on a spindle part of a dental drill, from the front end side or rear end side of the dental drill so as to regulate the depth of the hole.

2. Description of the Conventional Art

A dental implant treatment technique for fixing a dental prosthesis at a dental prosthesis maintaining device is developed and carried out. In a general dental implant treatment technique, an implant fixture as a maintaining and stabilizing device of the dental prosthesis is embedded into an implant fixture embedding hole formed in a jawbone at a defective tooth so as to act for a function of a tooth root of a natural tooth. Then, a dental prosthesis maintaining device is made by connecting and fixing a fixing device of a dental prosthesis on the intra-oral side of the implant fixture and the dental prosthesis is fixed to the dental prosthesis maintaining device.

In such the implant treatment, when an implant fixture embedding hole is bored in a jawbone at a defective tooth, a dental driving device, such as a hand piece or the like, having a dental drill having a spindle part and a blade part formed at the front end side of the spindle part is used, and the hole is bored in the jawbone at the defective tooth by the blade part of the dental drill. The spindle part has a diameter shrunk part, which is formed as a mounting part for preventing slipping-off to a dental hand piece, at a rear end thereof, or has a cylindrical shape having an equal diameter without having the diameter shrunk part.

However, if the implant fixture embedding hole formed by the aforementioned operation does not have a proper depth, there occurs a problem that a dental prosthesis cannot be fixed to the implant fixture embedded in the implant fixture embedding hole or the implant fixture cannot be stably embedded in the implant fixture embedding hole. In addition to this, there may be a trouble that the jawbone is damaged in the worst case. Therefore, in such the implant treatment, it is the most important thing that the implant fixture embedding hole is formed at an exact position in the jawbone at the defective tooth with an exact depth.

For this reason, for example, Japanese Translation of PCT Publication No. 2005-518834 (claims 1 and 11, etc.) discloses a method for arranging a dental implant by using a drill with a flange. That is, the method includes the step of producing a template by downloading a tomography of a jawbone of a patient to a computer, and by forming therein a hole having a specified embedding direction of a fixture on the basis of data in which the embedding direction of the fixture is previously determined and a complete state of a prosthesis device including the fixture is correctly simulated. The method also includes use of a dental drill with a flange which is for regulating a depth of an implant fixture embedding hole and integrally formed with a spindle part.

As for the method by using the template and the dental drill with a flange, the position and direction of the implant fixture embedding hole are specified with the template, and the depth of the implant fixture embedding hole is regulated by positioning of the flange of the dental drill with a flange. Thus, it can be prevented that the position of the implant fixture embedding hole is deviated and the implant fixture embedding hole is not formed having a proper depth.

However, since the dental drill with a flange has a structure in which the flange for regulating the depth of the implant fixture embedding hole is formed integrally with the spindle part, in case of the method by using the template and the dental drill with a flange, there is a fault that several kinds of dental drills with a flange, each of which has only a different position in an axial direction of the flange corresponding to a depth of the implant fixture embedding hole, must be prepared, even though each of these dental drills with a flange has a completely same shape of a blade part. Further, generally, plural kinds of dental drills having different shapes of blade parts respectively must be prepared. Thus, there is a fault that vast kinds of dental drills with a flange, each of which has only a different position in an axial direction of the flange, must be prepared for every plural kinds of the blade parts. Therefore, an economic burden is great.

Furthermore, when the method by using the template and a dental drill with a flange is applied, a dental drill without a flange, which has been conventionally used widely, cannot be used. Thus, there is fault that a dentist needs to newly prepare vast kinds of dental drills with a flange, each of which has only a different position in an axial direction of the flange for every plural kinds of the blade parts. In addition, many general dental drills without a flange, which have been conventionally used widely, become useless.

SUMMARY OF THE INVENTION

Problem To Be Solved By The Invention

The present invention is directed to provide a detachable stopper for a dental drill so as to solve the aforementioned faults. The detachable stopper is externally fitted to and fixed at a position on a spindle part of a dental drill, which is for boring an implant fixture embedding hole in an implant treatment, from the front end side or rear end side of the dental drill and regulates a depth of a hole. The dental drill has a blade part at the front end side of the spindle part and the spindle part has a diameter shrunk part, which is formed as a mounting part for preventing slipping-off to a dental hand piece, at a rear end thereof, or is in a cylindrical shape having an equal diameter without having the diameter shrunk part. More particularly, the detachable stopper for a dental drill can maintain a state of being accurately fitted externally to the spindle part of the dental drill, and can be easily attached and detached.

Means for Solving the Problem

The present inventors carried out earnest works to solve the aforementioned problems and, as a result, they found out the followings to complete the present invention. A detachable stopper for a dental drill includes a stopper main body being made of an elastically deformable metal material, having a cylindrical shape, having a slightly smaller inner diameter than an outer diameter of a spindle part of a dental drill in a stationary state, having a slit part formed along an axial overall length thereof from an outer peripheral face to an inner peripheral face so as to have an opening, and having an diameter expanding tool insertion part bored at an axial center part of the slit part. The detachable stopper for a dental drill also includes a diameter expanding tool having a shape which can be freely inserted into and removed from the diameter expanding tool insertion part of the stopper main body, and being inserted into the diameter expanding tool insertion part of the stopper main body so as to expand the inner diameter of the stopper main body to be larger than the outer diameter of the spindle part of the dental drill. According to the structure mentioned above, when the diameter expanding tool is inserted into the diameter expanding tool insertion part of the stopper main body, the inner diameter of the stopper main body becomes in a diameter expanding state of being larger than the outer diameter of the spindle part of the dental drill, in a state in which the stopper main body can be inserted from the front end side or rear end side of the dental drill. On the other hand, when the diameter expanding tool is removed from the diameter expanding tool insertion part of the stopper main body, the inner diameter of the stopper main body becomes in a stationary state of being slightly smaller than the outer diameter of the spindle part of the dental drill, that is, in a state in which the stopper main body is externally fitted to and fixed to a position at the spindle part of the dental drill. Therefore, only by an easy operation of inserting/removing the diameter expanding tool into/from the diameter expanding tool insertion part of the stopper main body, the stopper main body can change to be in either the diameter expanding state or the stationary state. Thus, the stopper can maintain a state of being accurately fitted externally to the spindle part of the dental drill, and can be easily attached and detached.

An aspect of the present invention is a detachable stopper for a dental drill, which is externally fitted to and fixed at a position on a spindle part of a dental drill from the front end side or rear end side of the dental drill so as to regulate the depth of the hole, the dental drill being for boring an implant fixture embedding hole in an implant treatment and having a blade part at the front end side of the spindle part, the spindle part having a diameter shrunk part, which is formed as a mounting part for preventing slipping-off to a dental hand piece, at a rear end thereof, or being in a cylindrical shape having an equal diameter without having the diameter shrunk part, wherein the detachable stopper includes a stopper main body being made of an elastically deformable metal material, having a cylindrical shape, having a slightly smaller inner diameter than an outer diameter of the spindle part of the dental drill in a stationary state, having a slit part formed along an axial overall length from an outer peripheral face to an inner peripheral face so as to have an opening, and having a diameter expanding tool insertion part bored at an axial center part of the slit part, and also includes a diameter expanding tool having a shape capable of being freely inserted into and removed from the diameter expanding tool insertion part of the stopper main body, and being inserted into the diameter expanding tool insertion part of the stopper main body so as to expand the inner diameter of the stopper main body to be larger than the outer diameter of the spindle part of the dental drill.

As for the detachable stopper for a dental drill, the following structures are preferable for accurately expanding the inner diameter of the stopper main body. In one case, the diameter expanding tool insertion part of the stopper main body has a reduced portion, which is formed so as to have reduced cross section areas from an outer peripheral side toward an inner peripheral side and to have similar cross section shapes from the outer peripheral side to the inner peripheral side, and in addition, the front end side of the diameter expanding tool is formed so as to have a slightly larger cross section than the cross section at the inner peripheral side of the reduced portion of the diameter expanding tool insertion part of the stopper main body. In another case, the diameter expanding tool insertion part of the stopper main body is formed to have an approximately same cross section from the outer peripheral side to the inner peripheral side, and in addition, the front end side of the diameter expanding tool is formed to have cross section areas smaller than the cross section area of the diameter expanding tool insertion part of the stopper main body gradually toward a front end from a portion having a larger cross section area than the cross section area of the diameter expanding tool insertion part of the stopper main body. By taking these structures, the inner diameter of the stopper main body can be accurately expanded, so it is preferable. Further, in these structures, the diameter expanding tool insertion part of the stopper main body has a circular cross section and has a female screw on an inner face at the outer peripheral side, and in addition, the diameter expanding tool has a male screw to be screwed into the female screw of the diameter expanding tool insertion part of the stopper main body. In this case, when the diameter expanding tool is screwed into the diameter expanding tool insertion part of the stopper main body, the inner diameter of the stopper main body can be easily expanded, so it is preferable.

Further, a diameter expanding auxiliary portion recessed toward the inner peripheral side along an axial overall length can be formed on the outer peripheral face side of a portion opposite to the slit part beyond a center axis of the stopper main body. In such a structure, when the diameter expanding tool is inserted into the diameter expanding tool insertion part of the stopper main body, the inner diameter of the stopper main body can be easily expanded, so it is preferable. Furthermore, when the stopper main body is made of a titanium alloy, the material has biocompatibility required in an implant treatment, so it is preferable.

Effect of the Invention

The detachable stopper for a dental drill according to the present invention has the aforementioned structures. When the diameter expanding tool is inserted into the diameter expanding tool insertion part of the stopper main body, the inner diameter of the stopper main body becomes in a diameter expanding state of being larger than the outer diameter of the spindle part of the dental drill, that is, in a state in which the stopper main body can be inserted from the front end side or rear end side of the dental drill. On the other hand, when the diameter expanding tool is removed from the diameter expanding tool insertion part of the stopper main body, the inner diameter of the stopper main body becomes in a stationary state of being slightly smaller than the outer diameter of the spindle part of the dental drill, that is, in a state in which the stopper main body is externally fitted to and fixed at a position on the spindle part of the dental drill. Therefore, only by an easy operation of inserting/removing the diameter expanding tool into/from the diameter expanding tool insertion part of the stopper main body, the stopper main body can change to be either in the diameter expanding state or in the stationary state. Thus, the stopper main body can maintain a state of being accurately fitted externally to the spindle part of the dental drill, and can be easily attached and detached. In addition, even in a case of using a conventional general dental drill without a flange, when the stopper is externally fitted to the spindle part from the front end side or the rear end side and fixed at a position on the spindle part, the dental drill without a flange can be used as a dental drill which can regulate the depth of the implant fixture embedding hole, like a conventional dental drill with a flange. Therefore, many conventionally used general dental drills without a flange do not become useless and an economical burden can be greatly reduced.

Further, the implant fixture embedding hole having a proper depth can be bored only by changing the axial position of the stopper and fixing it, when the stopper is externally fitted to the spindle part of the dental drill. Thus, unlike a conventional dental drill with a flange, it is not necessary that plural kinds of dental drills with a flange, each of which has only a different axial position of the flange, are prepared corresponding to the depth of the implant fixture embedding hole.

Further, even when the plural kinds of the dental drills with a flange, each of which has only a different axial position of the flange, are prepared, such the conventional dental drills with a flange can only be applied to a stepped variety of depths of the implant fixture embedding hole. In contrast, the detachable stopper for a dental drill according to the present invention can be fixed at a freely changed axial position when the stopper main body is externally fitted to the spindle part of the dental drill. Thus, one dental drill can be freely applied continuously to depths of the implant fixture embedding hole.

Further, as for the detachable stopper for a dental drill, the following structures of the stopper main body and the diameter expanding tool are preferable for expanding the inner diameter of the stopper main body. In one structure, the diameter expanding tool insertion part of the stopper main body has a reduced portion, which is formed so as to have reduced cross section areas from an outer peripheral side toward an inner peripheral side, and to have similar cross section shapes from the outer peripheral side to the inner peripheral side, and in addition, the front end side of the diameter expanding tool is formed so as to have a slightly larger cross section than the cross section at the inner peripheral side of the reduced portion of the diameter expanding tool insertion part of the stopper main body. In another structure, the diameter expanding tool insertion part of the stopper main body is formed to have an approximately same cross section from the outer peripheral side to the inner peripheral side, and in addition, the front end side of the diameter expanding tool is formed to have cross section areas smaller than the cross section area of the diameter expanding tool insertion part of the stopper main body gradually toward a front end from a portion having a larger cross section area than the cross section area of the diameter expanding tool insertion part of the stopper main body. By taking these structures, the inner diameter of the stopper main body can be accurately expanded, so it is preferable. Further, in these structures, the diameter expanding tool insertion part of the stopper main body has the circular cross section and has the female screw on an inner face at the outer peripheral side, and in addition, the diameter expanding tool has the male screw to be screwed into the female screw of the diameter expanding tool insertion part of the stopper main body. In this case, when the diameter expanding tool is screwed into the diameter expanding tool insertion part of the stopper main body, the inner diameter of the stopper main body can be easily expanded, so it is preferable. In addition, by operating the diameter expanding tool to rotate around the axis thereof, the stopper main body can change to be either in the diameter expanding state or in the stationary state. Thus, the force required for expanding the inner diameter of the stopper main body can be reduced, so it is preferable.

Further, the diameter expanding auxiliary portion recessed toward the inner peripheral side along an axial overall length is formed on the outer peripheral face side of a portion opposite to the slit part beyond a center axis of the stopper main body. In such a structure, when the diameter expanding tool is inserted into the diameter expanding tool insertion part of the stopper main body, the inner diameter of the stopper main body is easily expanded, so it is preferable. In addition to this, the force required for operating to expand the inner diameter of the stopper main body can be reduced, so it is preferable. Further, the stopper main body can be stably put on a flat face, e.g., on a table, in a state that the diameter expanding tool insertion part is upwardly directed and the diameter expanding auxiliary portion contacts to the flat face, e.g., to a table. Thus, when the stopper main body is put on the flat face, e.g., on a table at a time of inserting/removing the diameter expanding tool into/from the diameter expanding tool insertion part of the stopper main body, the handling of the inserting and removing can be easily carried out, so it is preferable. Furthermore, when the stopper main body is made of a titanium alloy, the material has biocompatibility required in an implant treatment. In a case of boring the implant fixture embedding hole without using a template having a hole formed to have a specified embedding direction of a fixture, when the stopper main body directly contacts to a living body such as a gingiva, the influence given to a living body can be reduced, so it is preferable. In addition, since durability can be improved, it is preferable.

DETAILED DESCRIPTION OF PREFERRED EMBODIMENT

A detachable stopper for a dental drill according to the present invention will be described in detail below with reference to drawings.

In these drawings, a stopper main body 1 is made of an elastically deformable metal material, has a cylindrical shape, has a slightly smaller inner diameter than an outer diameter of a spindle part D3 of a dental drill D in a stationary state, has a slit part 1*a* formed along an axial overall length from an outer peripheral face to an inner peripheral face so as to have an opening, and has a diameter expanding tool insertion part 1*b* bored at an axial center part of the slit part 1*a*. The stopper main body 1 is externally fitted from the front end side or rear end side of the dental drill D and fixed at a position on the spindle part D3 of the dental drill D so as to regulate a depth of an implant fixture embedding hole.

Figure 5:
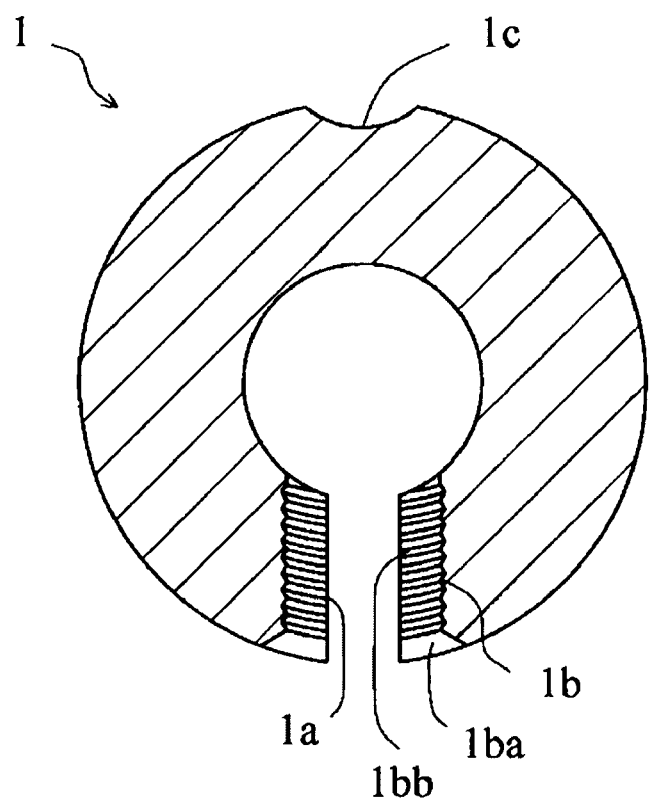
FIG. 5 is an explanatory sectional view taken along line A-A in FIG. 2.
Figure 6:
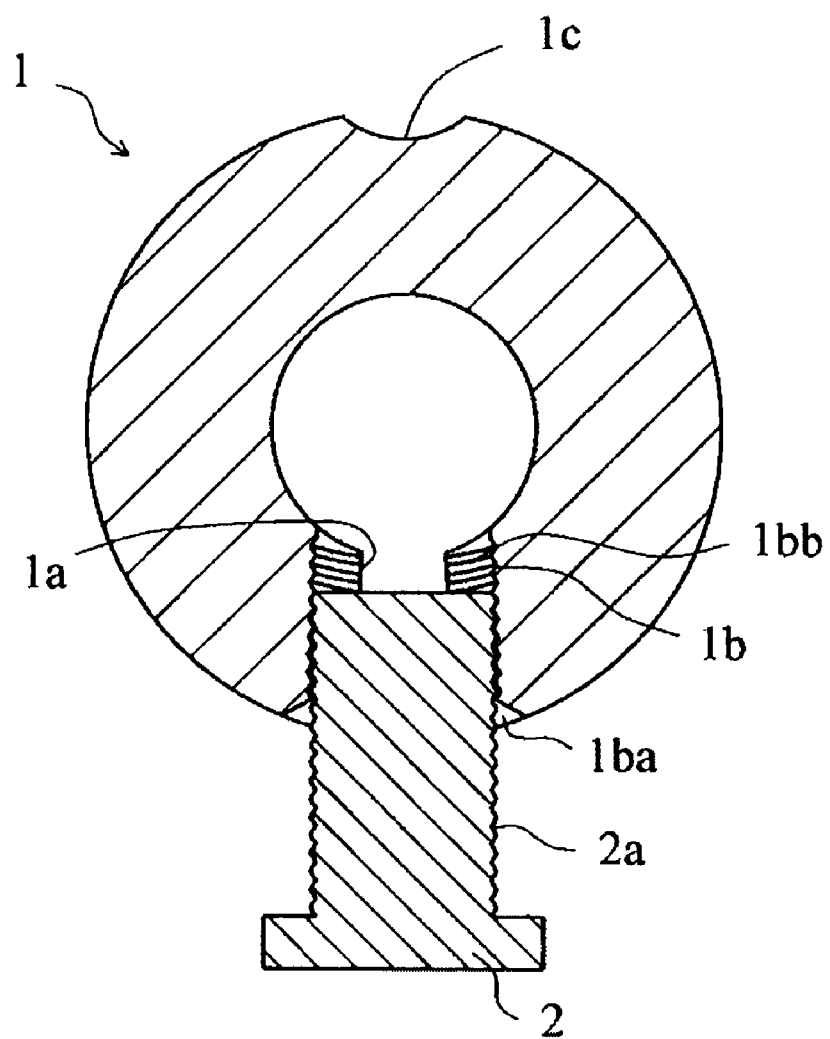
FIG. 6 is an explanatory sectional view to illustrate a state in which one example of a diameter expanding tool is inserted into a diameter expanding tool insertion part of a stopper main body illustrated in FIG. 5 so as to expand an inner diameter of the stopper main body.
Figure 9:
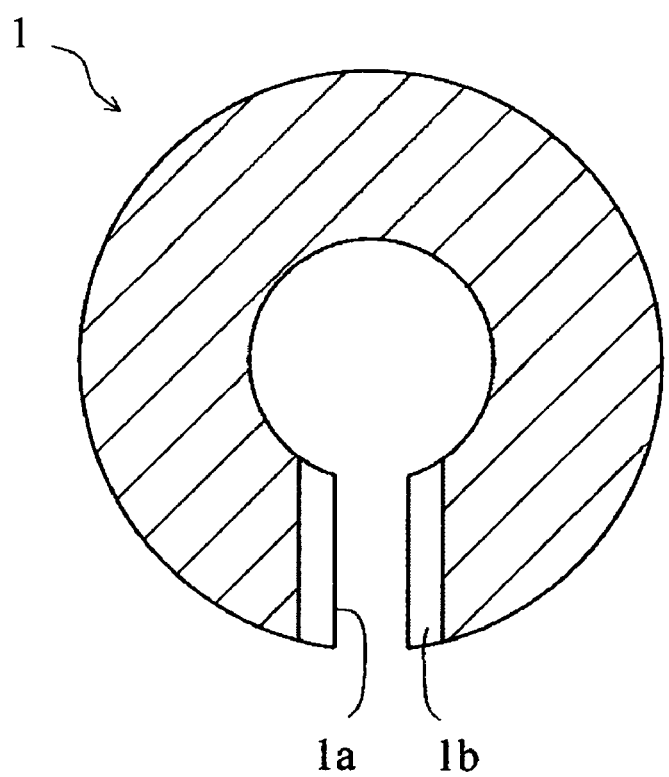
FIG. 9 is an explanatory sectional view taken along line B-B in FIG. 7.
Figure 10:
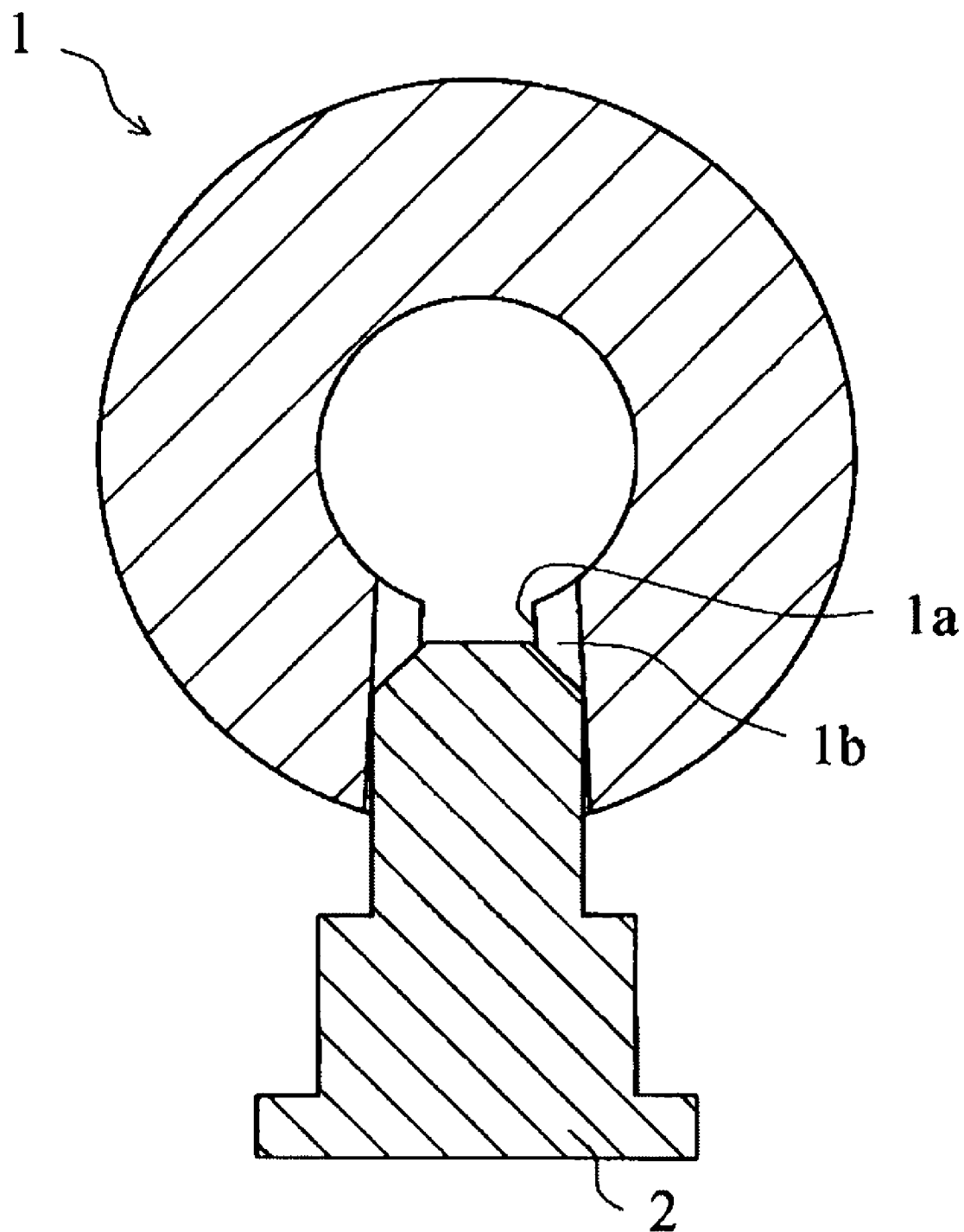
FIG. 10 is an explanatory sectional view to illustrate a state in which another example of a diameter expanding tool is inserted into a diameter expanding tool insertion part of a stopper main body illustrated in FIG. 9 so as to expand an inner diameter of the stopper main body.
Figure 11:
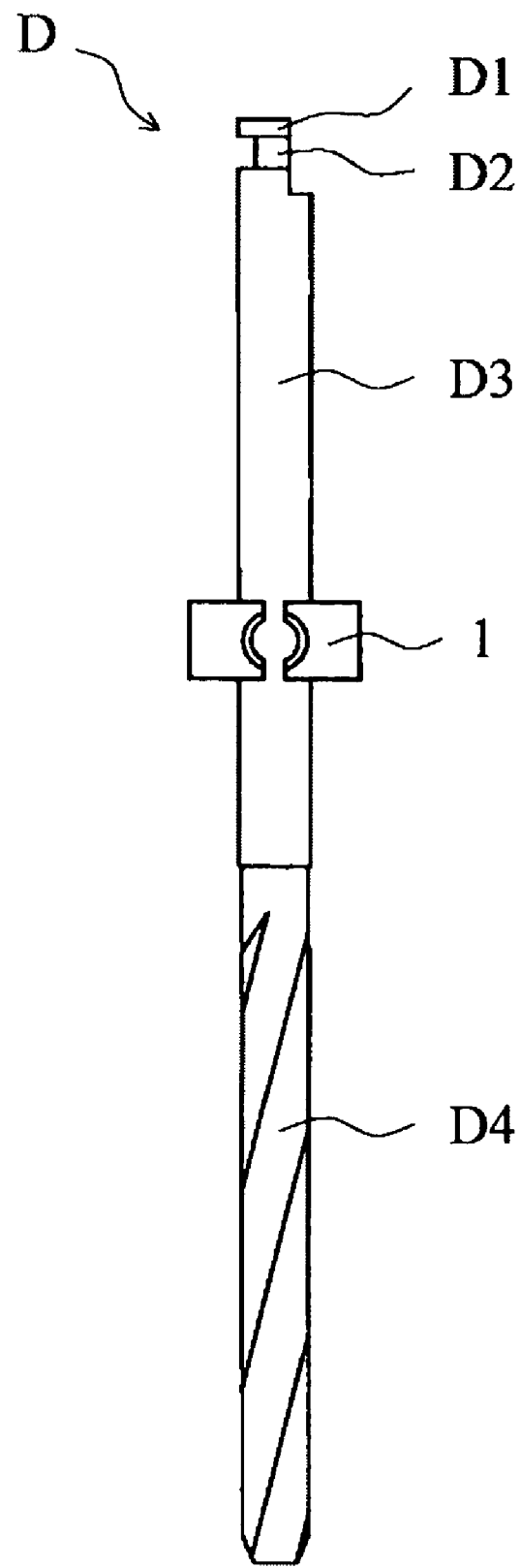
FIG. 11 is an explanatory front view to illustrate a state in which another example of a stopper main body in a detachable stopper for a dental drill according to the present invention is externally fitted to and fixed at a position on a spindle part of a dental drill.

As illustrated in FIGS. 1, 2, and 4 to 11, the stopper main body 1 has a cylindrical shape and has the slit part 1a which is formed along the axial overall length from the outer peripheral face to the inner peripheral face thereof so as to have an opening. The stopper main body 1 has the diameter expanding tool insertion part 1b bored at the axial center part of the slit part 1a. Further, when the stopper main body 1 is externally fitted to and fixed at a position on the spindle part D3 of the dental drill D as illustrated in FIG. 11, the inner diameter of the stopper main body 1 is expanded to be larger than the outer diameter of the spindle D3 of the dental drill D so as to make a diameter expanding state in which the stopper main body 1 can be fitted from the front end side or rear end side of the dental drill D, by inserting a diameter expanding tool 2 described below into the diameter expanding tool insertion part 1b of the stopper main body 1 as illustrated in FIGS. 6 and 10, because the inner diameter of the stopper main body 1 is slightly smaller than the outer diameter of the spindle part D3 of the dental drill D in the stationary state as illustrated in FIGS. 5 and 9. In this state, the stopper main body 1 with the diameter expanding tool 2 inserted therein can be fitted from the front end side or rear end side of the dental drill D and moved to a proper position on the spindle D3 of the dental drill D.

Further, the stopper main body 1 is made of an elastically deformable metal material. Thus, after the stopper main body 1 with the diameter expanding tool 2 inserted therein is inserted from the front end side or rear end side of the dental drill D and moved to a proper position on the spindle D3 of the dental drill D, the inner diameter is returned to the stationary state, of being slightly smaller than the outer diameter of the spindle part D3 of the dental drill D, by elastic deformation force of the metal material, when the diameter expanding tool 2 is removed from the diameter expanding tool insertion part 1b of the stopper main body 1. Thus, the stopper main body 1 can keep a state of being accurately fitted externally to and fixed on the spindle part D3 of the dental drill D by the elastic deformation force. On the other hand, when the stopper main body 1 which is accurately fitted externally to and fixed on the spindle part D3 of the dental drill D is removed from the dental drill D, the diameter expanding tool 2 described below is inserted into the diameter expanding tool insertion part 1b of the stopper main body 1 as illustrated in FIGS. 6 and 10. By this operation, the inner diameter of the stopper main body 1 is expanded to be larger than the outer diameter of the spindle part D3 of the dental drill D so as to make the diameter expanding state in which the stopper main body 1 can be inserted from the front end side or rear end side of the dental drill D. Then, the stopper main body 1 with the diameter expanding tool 2 inserted therein can be pulled out from the front end side or rear end side of the dental drill D.

As illustrated in FIGS. 1, 2, and 4 to 11, the stopper main body 1 has the slit part 1a formed along the axial overall length from the outer peripheral face to the inner peripheral face. Owing to the slit part 1a having such the structure, the stopper main body 1 can change to be either in the stationary state in which the inner diameter of the stopper main body 1 is slightly smaller than the outer diameter of the spindle part D3 of the dental drill D as illustrated in FIGS. 5 and 9, or in the diameter expanding state in which the inner diameter of the stopper main body 1 is larger than the outer diameter of the spindle part D3 of the dental drill D, that is, the width of the slit part 1a is deformed to be larger than that in the stationary state, as illustrated in FIGS. 6 and 10.

Figure 1:
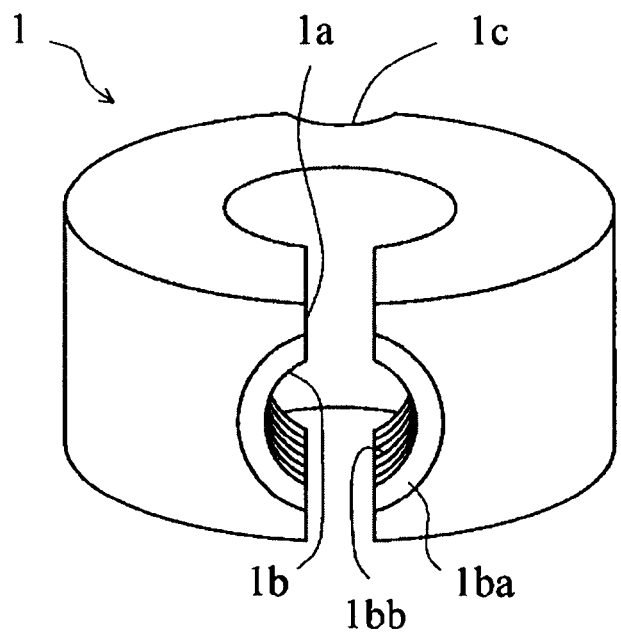
FIG. 1 is a explanatory perspective view to illustrate one example of a stopper main body in a detachable stopper for a dental drill according to the present invention.
Figure 2:
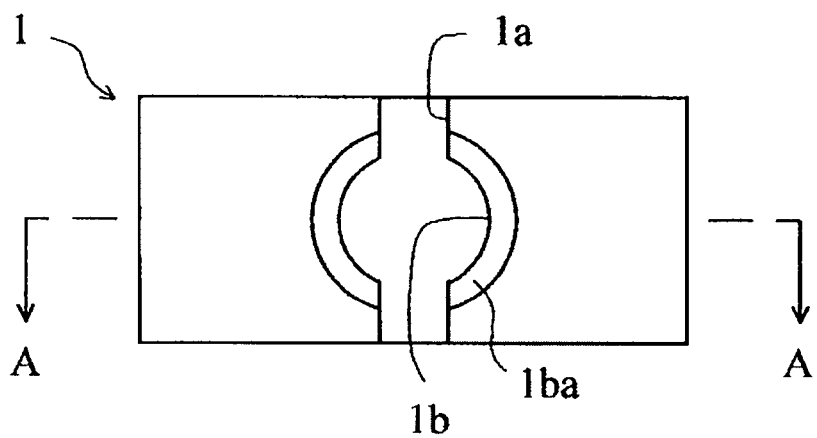
FIG. 2 is an explanatory front view of FIG. 1.
Figure 3:
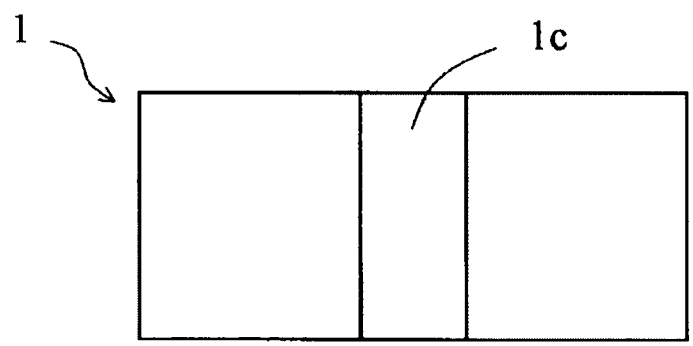
FIG. 3 is an explanatory rear view of FIG. 1.
Figure 4:
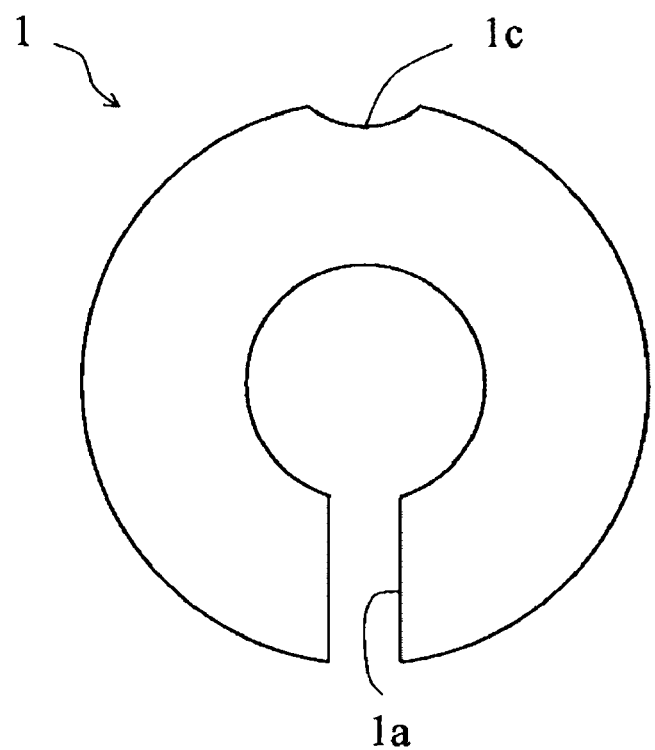
FIG. 4 is an explanatory plan view of FIG. 1.
Figure 7:
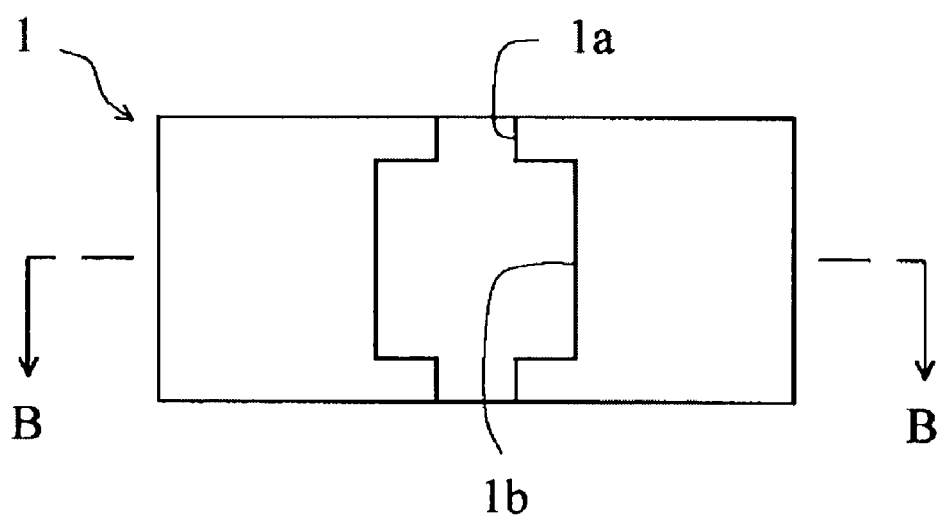
FIG. 7 is an explanatory front view to illustrate another example of a stopper main body in a detachable stopper for a dental drill according to the present invention.
Figure 8:
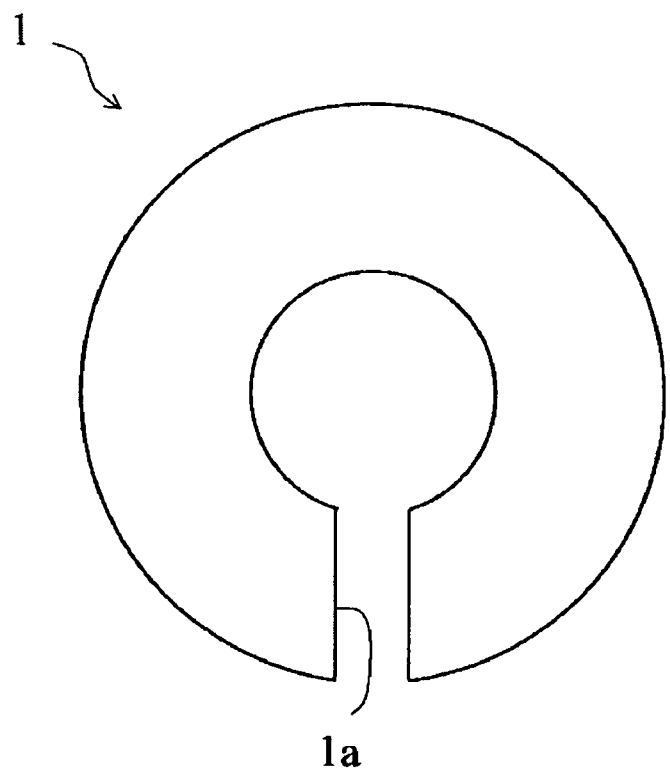
FIG. 8 is an explanatory plan view of FIG. 7.

As illustrated in FIGS. 1, 2, 5 to 7, and 9 to 11, the diameter expanding tool insertion part 1b is bored at the axial center part of the slit part 1a of the stopper main body 1. The diameter expanding tool insertion part 1b can have any shapes, if the shape corresponds to a shape of the diameter expanding tool 2 so that the inner diameter of the stopper main body 1 can be expanded to be larger than the outer diameter of the spindle part D3 of the dental drill D by inserting the diameter expanding tool 2 described below into it. For example, the diameter expanding tool insertion part 1b can have a circular cross section when seeing it from the outer peripheral face side as illustrated in FIGS. 1, 2, and 11, or have a rectangular cross section when seeing it from the outer peripheral face side as illustrated in FIG. 7.

Further, as for the diameter expanding tool insertion part 1b of the stopper main body 1, the following structures are preferable for accurately expanding the inner diameter of the stopper main body. In one structure, the diameter expanding tool insertion part 1b of the stopper main body 1 has a reduced portion 1ba, which is formed to have reduced cross section areas from an outer peripheral side toward an inner peripheral side and to have similar cross section shapes from the outer peripheral side to the inner peripheral side, as illustrated in FIGS. 1, 2, 5, and 6, and in addition, the front end side of the diameter expanding tool 2 described below is formed so as to have a slightly larger cross section than the cross section at the inner peripheral side of the reduced portion 1ba of the diameter expanding tool insertion part 1b of the stopper main body 1. In another structure, as illustrated in FIGS. 7, 9, and 10, the diameter expanding tool insertion part 1b of the stopper main body 1 is formed so as to have an approximately same cross section from the outer peripheral side to the inner peripheral side, and in addition, the front end side of the diameter expanding tool 2 described below is formed so as to have cross section areas smaller than a cross section area of the diameter expanding tool insertion part 1b of the stopper main body 1 gradually toward a front end from a portion having a larger cross section area than the cross section area of the diameter expanding tool insertion part 1b of the stopper main body 1. By taking these structures, the inner diameter of the stopper main body 1 can be accurately expanded, so it is preferable.

Further, in the diameter expanding tool insertion part 1b of the stopper main body 1 having the aforementioned structure and the diameter expanding tool 2 described below, as illustrated in FIGS. 1, 5, and 6, the diameter expanding tool insertion part 1b of the stopper main body 1 has a circular cross section and has a female screw 1bb formed on the inner face at the outer peripheral side, and in addition, the diameter expanding tool 2 has a male screw 2a to be screwed into the female screw 1bb of the diameter expanding tool insertion part 1b of the stopper main body 1. Thus, only by screwing the diameter expanding tool 2 into the diameter expanding tool insertion part 1b of the stopper main body 1, the inner diameter of the stopper main body 1 can be expanded easily, so it is preferable. In addition, when the diameter expanding tool 2 is rotated around the axis thereof, the stopper main body 1 can change to be either in the diameter expanding state or in the stationary state. Thus, the force needed for an operation for expanding the inner diameter of the stopper main body 1 can be reduced, so it is preferable.

Further, as illustrated in FIGS. 1, and 3 to 6, a diameter expanding auxiliary portion 1c recessed toward the inner peripheral face side along the axial overall length is formed on the outer peripheral face side of a portion at the opposite side of the slit part 1*a* beyond the center axis of the stopper main body 1. Thus, when the diameter expanding tool 2 is inserted into the diameter expanding tool insertion part 1*b* of the stopper main body 1, the inner diameter of the stopper main body 1 can be expanded easily, so it is preferable. In addition, force needed for an operation for expanding the inner diameter of the stopper main body 1 can be reduced, so it is preferable. Further, the stopper main body 1 can be stably put on a flat face, e.g., on a table, in a state that the diameter expanding tool insertion part 1*b* is upwardly directed and the diameter expanding auxiliary portion 1*c* contacts to the flat face, e.g., to a table. Thus, when the diameter expanding tool 2 is inserted into and removed from the diameter expanding tool insertion part 1*b* of the stopper main body 1, the diameter expanding tool 2 can be easily inserted and removed in the state that the stopper main body 1 is put on the flat face, e.g., on a table, so it is preferable.

The material of the stopper main body 1 is not restricted especially if it is made of the elastically deformable metal material, that is, a general metallic material such as stainless or aluminum. However, if the stopper main body 1 is made of a titanium alloy, the material has biocompatibility required in an implant treatment. Thus, in a case that the implant fixture embedding hole is bored without using a template having a hole by which the embedding direction of the fixture is specified, when the stopper main body 1 is directly contacted with a living body such as a gingiva, the influence given to a living body can be reduced, so it is preferable. In addition, since durability can be improved, it is preferable.

A diameter expanding tool 2 has a shape capable of being freely inserted into and removed from the diameter expanding tool insertion part 1*b* of the stopper main body 1, and is inserted into the diameter expanding tool insertion part 1*b* of the stopper main body 1 so as to expand the inner diameter of the stopper main body 1 to be larger than the outer diameter of the spindle part D3 of the dental drill D. The diameter expanding tool 2 is inserted into the diameter expanding tool insertion part 1*b* of the stopper main body 1 so as to make the diameter expanding state in which the inner diameter of the stopper main body 1 becomes larger than the outer diameter of the spindle part D3 of the dental drill D, that is, the state in which the stopper main body 1 can be inserted from the front end side or rear end side of the dental drill D. Further, the diameter expanding tool 2 is removed from the diameter expanding tool insertion part 1*b* of the stopper main body 1 so as to make the stationary state in which the inner diameter of the stopper main body 1 becomes slightly smaller than the outer diameter of the spindle part D3 of the dental drill D, that is, the state in which the stopper main body 1 is externally fitted to and fixed at a position on the spindle part D3 of the dental drill D.

The diameter expanding tool 2 is not restricted if it has a shape which allows it to be freely inserted into and removed from the diameter expanding tool insertion part 1*b* of the stopper main body 1 and which corresponds to the shape of the diameter expanding tool insertion part 1*b* of the stopper main body 1 so that it can be inserted into the diameter expanding tool insertion part 1*b* of the stopper main body 1 to expand the inner diameter of the stopper main body 1 to be larger than the outer diameter of the spindle part D3 of the dental drill D. For example, as illustrated in FIGS. 1, 2, and 11, if the diameter expanding tool insertion part 1*b* of the stopper main body 1 has a circular cross section when seeing it from the outer peripheral face side, the diameter expanding tool 2 similarly has a circular cross section, although this shape is not illustrated. Further, as illustrated in FIG. 7, if the diameter expanding tool insertion part 1*b* of the stopper main body 1 has a rectangular cross section when seeing it from the outer peripheral face side, the diameter expanding tool 2 similarly has a rectangular cross section, although this shape is not illustrated.

Further, as one shape of the diameter expanding tool 2, for example, when the diameter expanding tool insertion part 1*b* of the stopper main body 1 has a reduced portion 1*ba*, which is formed so as to have reduced cross section areas from an outer peripheral side toward an inner peripheral side and to have similar cross section shapes from the outer peripheral side to the inner peripheral side, as illustrated in FIGS. 1, 2, 5, and 6, the front end side of the diameter expanding tool 2 is formed so as to have a slightly larger cross section than the cross section at the inner peripheral side of the reduced portion 1*ba* of the diameter expanding tool insertion part 1*b* of the stopper main body 1. As another shape of the diameter expanding tool, when the diameter expanding tool insertion part 1*b* of the stopper main body 1 has the approximately same cross section from the outer peripheral side to the inner peripheral side, as illustrated in FIGS. 7, 9 and 10, the front end side of the diameter expanding tool 2 is formed so as to have cross section areas smaller than the cross section area of the diameter expanding tool insertion part 1*b* of the stopper main body 1 gradually toward the front end from the portion having the larger cross section area than the cross section area of the diameter expanding tool insertion part 1*b* of the stopper main body 1. Owing to those structures, the inner diameter of the stopper main body 1 can be accurately expanded, so it is preferable.

In particular, in a case of the structure as illustrated in FIGS. 1, 2, 5, and 6, the diameter expanding tool 2 is formed to have the front end side which has the slightly larger cross section than the cross section at on the inner peripheral side of the reduced portion 1*ba* of the diameter expanding tool insertion part 1*b* of the stopper main body 1, and the front end side is inserted, from the outer peripheral side toward the inner peripheral side, into the diameter expanding tool insertion part 1*b* of the stopper main body 1 having the reduced portion 1*ba*, which has the reduced cross section areas from the outer peripheral side toward the inner peripheral side and has similar cross section shapes from the outer peripheral side to the inner peripheral side. Then, as illustrated in FIG. 6, the front end side of the diameter expanding tool 2 gradually pushes and expands the slit part 1*a* while contacting to the reduced portion 1*ba* of the diameter expanding tool insertion part 1*b* of the stopper main body 1. Thus, the inner diameter of the stopper main body 1 can be accurately expanded, so it is preferable. In addition, the force required for expanding the inner diameter of the stopper main body can be reduced, so it is preferable.

On the other hand, in a case of the structure as illustrated in FIGS. 7, 9, and 10, the diameter expanding tool 2 is formed to have the front end side which has the cross section areas smaller than the cross section area of the diameter expanding tool insertion part 1*b* of the stopper main body 1 gradually toward the front end from the portion having the larger cross section area than the cross section area of the diameter expanding tool insertion part 1*b* of the stopper main body 1, and the front end side is inserted, from the outer peripheral side toward the inner peripheral side, into the diameter expanding tool insertion part 1*b* of the stopper main body 1, which is formed to have the approximately same cross section from the outer peripheral side to the inner peripheral side. Then, as illustrated in FIG. 10, a portion at the front end side of the diameter expanding tool 2 (a tapered portion in FIG. 10) gradually pushes and expands the slit part 1*a* while contacting to the outer peripheral side of the diameter expanding tool insertion part 1*b* of the stopper main body 1. Thus, the inner diameter of the stopper main body 1 can be accurately expanded, so it is preferable. In addition, the force required for expanding the inner diameter of the stopper main body can be reduced, so it is preferable.

Further, in the diameter expanding tool insertion part 1*b* of the stopper main body 1 and the diameter expanding tool 2 having the aforementioned structures, the diameter expanding tool insertion part 1*b* of the stopper main body 1 has the circular cross section and has the female screw 1*bb* formed on the inner face at the outer peripheral side, and the diameter expanding tool 2 has the male screw 2*a* to be screwed into the female screw 1*bb* of the diameter expanding tool insertion part 1*b* of the stopper main body 1, as illustrated in FIGS. 1, 5, and 6. In such the structure, by screwing the diameter expanding tool 2 into the diameter expanding tool insertion part 1*b* of the stopper main body 1, the inner diameter of the stopper main body 1 can be expanded easily, so it is preferable. In addition to this, by the operation that the diameter expanding tool 2 is rotated around the axis thereof, the stopper main body 1 can change to be in either the diameter expanding state or the stationary state, and thereby the force required for expanding the inner diameter of the stopper main body can be reduced, so it is preferable.

Furthermore, the diameter expanding tool 2 can have a screw part having a self-tapping function at the front end side thereof, although it is not illustrated. In such the case, when the diameter expanding tool 2 is screwed into the diameter expanding tool insertion part 1*b* of the stopper main body 1, the female screw 1*bb* is simultaneously formed on the inner face of the diameter expanding tool insertion part 1*b* of the stopper main body 1. Thus, a time and work for previously forming the female screw 1*bb* at the diameter expanding tool insertion part 1*b* of the stopper main body 1 can be saved, so it is preferable.

Then, a use method of the detachable stopper for a dental drill according to the present invention having the aforementioned structure will be described.

First, the diameter expanding tool 2 is inserted into the diameter expanding tool insertion part 1*b* of the stopper main body 1 in order to make the diameter expanding state in which the inner diameter of the stopper main body 1 is expanded to be larger than the outer diameter of the spindle part D3 of the dental drill D, as illustrated in FIGS. 6 and 10.

As for this inserting operation, more particularly, for example, when the diameter expanding tool insertion part 1*b* of the stopper main body 1 does not have the female screw 1*bb* and the diameter expanding tool 2 does not have the male screw 2*a* or the screw part having the self-tapping function as illustrated in FIGS. 7 to 10, the front end side of the diameter expanding tool 2 is inserted, from the outer peripheral side to the inner peripheral side, into the diameter expanding tool insertion part 1*b* of the stopper main body 1. Further, when the diameter expanding tool insertion part 1*b* of the stopper main body 1 has the female screw 1*bb* and the diameter expanding tool 2 has the male screw 2*a* as illustrated in FIGS. 1 to 6, the male screw 2*a* of the diameter expanding tool 2 is screwed, from the outer peripheral side to the inner peripheral side, into the female screw 1*bb* of the diameter expanding tool insertion part 1*b* of the stopper main body 1. Further, when the diameter expanding tool insertion part 1*b* of the stopper main body 1 does not have the female screw 1*bb* and the diameter expanding tool 2 has the screw part having the self-tapping function at the front end side thereof, although this state is not illustrated, the screw part having the self-tapping function of the diameter expanding tool 2 is screwed, from the outer peripheral side to the inner peripheral side, into the diameter expanding tool insertion part 1*b* of the stopper main body 1 while forming the female screw.

The inserting operation makes the diameter expanding state in which the inner diameter of the stopper main body 1 is expanded to be larger than the outer diameter of the spindle part D3 of the dental drill D, as illustrated in FIGS. 6 and 10. Thus, the stopper main body 1 changes to be in the state in which the stopper main body can be inserted from the front end side or the rear end side of the dental drill D. In addition, the inserting operation can be carried out previously or just before externally fitting the detachable stopper for a dental drill according to the present invention to the spindle part D3 of the dental drill D.

Then, the stopper main body 1 in the state of having the inner diameter expanded to be larger than the outer diameter of the spindle part D3 of the dental drill D by inserting the diameter expanding tool 2, is inserted from the front end side or the rear end side of the dental drill D and moved to a proper position on the spindle part D3 of the dental drill D.

At this time, since being in the diameter expanding state in which the inner diameter of the stopper main body 1 is expanded to be larger than the outer diameter of the spindle part D3 of the dental drill D as illustrated in FIGS. 6 and 10, the stopper main body 1 can be easily inserted from the front end side or the rear end side of the dental drill D and moved to the proper position on the spindle part D3 of the dental drill D.

Last, by removing the diameter expanding tool 2 from the stopper main body 1, which has been moved to the proper position on the spindle part D3 of the dental drill D, the stopper main body 1 is externally fitted to and fixed at the proper position on the spindle part D3 of the dental drill D as illustrated in FIG. 11.

As for this operation, more particularly, for example, when the diameter expanding tool insertion part 1*b* of the stopper main body 1 does not have the female screw 1*bb* and the diameter expanding tool 2 does not have the male screw 2*a* or the screw part having the self-tapping function as illustrated in FIGS. 7 to 10, the diameter expanding tool 2 inserted into the diameter expanding tool insertion part 1*b* of the stopper main body 1 is pulled out. Further, when the diameter expanding tool insertion part 1*b* of the stopper main body 1 has the female screw 1*bb* and the diameter expanding tool 2 has the male screw 2*a* as illustrated in FIGS. 1 to 6, or when the diameter expanding tool insertion part 1*b* of the stopper main body 1 does not have the female screw 1*bb* and the diameter expanding tool 2 has the screw part having the self-tapping function at the front end side thereof, although this state is not illustrated, the diameter expanding tool 2 inserted into the diameter expanding tool insertion part 1*b* of the stopper main body 1 is rotated around the axis thereof in a reverse direction to a screwing-in direction.

At this time, when the diameter expanding tool 2 is pulled out from the stopper main body 1, the stopper main body 1 is returned to the stationary state in which the inner diameter thereof is slightly smaller than the outer diameter of the spindle part D3 of the dental drill D by the elastic deformation force of the stopper main body 1. Thus, the stopper main body 1 can keep a state of being accurately fitted externally to the spindle part D3 of the dental drill D by the elastic deformation force.

Accordingly, after the detachable stopper for a dental drill according to the present invention is externally fitted to and fixed at the proper position on the spindle part D3 of the dental drill D, an operation for boring the implant fixture embedding hole in a jawbone at a defective tooth is carried out in an implant treatment. Thus, the implant fixture embedding hole can be formed so as to have an accurate depth.

Further, when the stopper main body 1 is required to be removed from the dental drill D or the position of the stopper main body 1 externally fitted to the spindle part D3 of the dental drill D is required to be changed after carrying out the operation for boring the implant fixture embedding hole, the stopper main body 1 can be in the diameter expanding state, in which the inner diameter of the stopper main body 1 is expanded to be larger than the outer diameter of the spindle part D3 of the dental drill D, only by inserting the diameter expanding tool 2 into the diameter expanding tool insertion part 1b of the stopper main body 1, as illustrated in FIGS. 6 and 10. Therefore, the stopper main body 1 can be easily removed, or the position of the stopper main body 1 can be easily changed.

What is claimed is:

1. A detachable stopper for a dental drill to be externally fitted to and fixed at a position on a spindle part of a dental drill from a front end side or a rear end side of the dental drill so as to regulate a depth of a drilled hole, the dental drill usable for boring an implant fixture embedding hole in an implant treatment, and the dental drill having a blade part at a front end side of the spindle part, the spindle part having a diameter shrunk part formed as a mounting part for preventing slipping-off a dental hand piece at a rear end thereof, or the spindle part being in a cylindrical shape having an equal diameter without having the diameter shrunk part, the detachable stopper comprising:
   a stopper main body being made of an elastically deformable metal material, the stopper main body having a cylindrical shape, having a bore with an inner diameter smaller than an outer diameter of the spindle part of the dental drill in a stationary state, having a slit part formed along an axial overall length from an outer peripheral face to an inner peripheral face of the stopper main body as an opening to the bore, and having a diameter expanding tool insertion part bored through an axial center part of the slit part; and
   a diameter expanding tool having a shape so that the diameter expanding tool is freely insertable into and removable from the diameter expanding tool insertion part of the stopper main body, the diameter expanding tool, when inserted into the diameter expanding tool insertion part, expands the inner diameter of the bore of the stopper main body to be larger than the outer diameter of the spindle part of the dental drill so that the stopper main body is movable along the spindle part, and the diameter expanding tool, when removed from the diameter expanding tool insertion part while the bore surrounds the spindle part, enables the inner diameter of the bore to contract to be externally fitted to and fixed on the spindle part.

2. The detachable stopper for a dental drill as claimed in claim 1,
   wherein the diameter expanding tool insertion part of the stopper main body has a reduced portion formed to have reduced cross section areas from an outer peripheral side toward an inner peripheral side, and to have similar cross section shapes from the outer peripheral side toward the inner peripheral side, and
   wherein a front end side of the diameter expanding tool is formed so as to have a larger cross section area than the cross section area of the reduced portion at the inner peripheral side of the reduced portion.

3. The detachable stopper for a dental drill as claimed in claim 2,
   wherein the diameter expanding tool insertion part of the stopper main body has a circular cross section shape and has a female screw on an inner face of the diameter expanding tool insertion part, and
   wherein the diameter expanding tool has a male screw to be screwed into the female screw of the diameter expanding tool insertion part.

4. The detachable stopper for a dental drill as claimed in claim 1,
   wherein the diameter expanding tool insertion part of the stopper main body is formed to have an approximately same cross section area from an outer peripheral side to an inner peripheral side, and
   wherein a front end side of the diameter expanding tool is formed to have cross section areas gradually smaller than the cross section area of the diameter expanding tool insertion part toward a front end of the diameter expanding tool from a portion of the diameter expanding tool having a larger cross section area than the cross section area of the diameter expanding tool insertion part.

5. The detachable stopper for a dental drill as claimed in claim 1,
   wherein the diameter expanding tool insertion part of the stopper main body has a circular cross section shape and has a female screw on an inner face of the diameter expanding tool insertion part, and
   wherein the diameter expanding tool has a male screw to be screwed into the female screw of the diameter expanding tool insertion part.

6. The detachable stopper for a dental drill as claimed in claim 1,
   wherein the stopper main body is made of a titanium alloy.

7. The detachable stopper for a dental drill as claimed in claim 1,
   wherein the diameter expanding tool insertion part of the stopper main body has a rectangular cross section shape.

8. A detachable stopper for a dental drill to be externally fitted to and fixed at a position on a spindle part of a dental drill from a front end side or a rear end side of the dental drill so as to regulate a depth of a drilled hole, the dental drill usable for boring an implant fixture embedding hole in an implant treatment, and the dental drill having a blade part at a front end side of the spindle part, the spindle part having a diameter shrunk part formed as a mounting part for preventing slipping-off a dental hand piece at a rear end thereof, or the spindle part being in a cylindrical shape having an equal diameter without having the diameter shrunk part, the detachable stopper comprising:
   a stopper main body being made of an elastically deformable metal material, the stopper main body having a cylindrical shape, having a bore with an inner diameter smaller than an outer diameter of the spindle part of the dental drill in a stationary state, having a slit part formed along an axial overall length from an outer peripheral face to an inner peripheral face of the stopper main body as an opening to the bore, and having a diameter expanding tool insertion part bored through an axial center part of the slit part,
   wherein the stopper main body has a diameter expanding auxiliary portion recessed toward the inner peripheral face along the axial overall length that is formed on the outer peripheral face of a portion of the stopper main body opposite to the slit part beyond a center axis of the stopper main body; and
   a diameter expanding tool having a shape so that the diameter expanding tool is freely insertable into and removable from the diameter expanding tool insertion part of the stopper main body, the diameter expanding tool, when inserted into the diameter expanding tool insertion part, expands the inner diameter of the bore of the stopper main body to be larger than the outer diameter of the spindle part of the dental drill.

9. The detachable stopper for a dental drill as claimed in claim 8, wherein the diameter expanding tool insertion part extends from the outer peripheral face to the inner peripheral face of the stopper main body, and the diameter expanding tool insertion part is wider than a width of the slit part.

10. A dental drilling system usable for boring an implant fixture embedding hole in an implant treatment, comprising:
   a dental drill, the dental drill including a spindle part, and the dental drill having a blade part at a front end side of the spindle part, the spindle part having a diameter shrunk part formed as a mounting part for preventing slipping-off a dental hand piece at a rear end thereof, or the spindle part being in a cylindrical shape having an equal diameter without having the diameter shrunk part; and
   a detachable stopper to be externally fitted to and fixed at a position on the spindle part of the dental drill from a front end side or a rear end side of the dental drill, so as to regulate a depth of a drilled hole, the detachable stopper including
      a stopper main body being made of an elastically deformable metal material, the stopper main body having a cylindrical shape, having a bore with an inner diameter smaller than an outer diameter of the spindle part of the dental drill in a stationary state, having a slit part formed along an axial overall length from an outer peripheral face to an inner peripheral face of the stopper main body as an opening to the bore, and having a diameter expanding tool insertion part bored through an axial center part of the slit part, and
      a diameter expanding tool having a shape so that the diameter expanding tool is freely insertable into and removable from the diameter expanding tool insertion part of the stopper main body, the diameter expanding tool, when inserted into the diameter expanding tool insertion part, expands the inner diameter of the bore of the stopper main body to be larger than the outer diameter of the spindle part of the dental drill so that the stopper main body is movable along the spindle part, and the diameter expanding tool, when removed from the diameter expanding tool insertion part while the bore surrounds the spindle part, enables the inner diameter of the bore to contract to be externally fitted to and fixed on the spindle part.

11. The detachable stopper for a dental drill as claimed in claim 1, wherein the diameter expanding tool insertion part extends from the outer peripheral face to the inner peripheral face of the stopper main body, and the diameter expanding tool insertion part is wider than a width of the slit part.

12. The dental drilling system as claimed in claim 10, wherein the diameter expanding tool insertion part extends from the outer peripheral face to the inner peripheral face of the stopper main body, and the diameter expanding tool insertion part is wider than a width of the slit part.

* * * * *